(12) United States Patent
Duncan et al.

(10) Patent No.: US 6,933,388 B2
(45) Date of Patent: Aug. 23, 2005

(54) PROCESS FOR THE SYNTHESIS OF 3-CYANO-6-ALKOXY-7-NITRO-4-QUINOLONES

(75) Inventors: Scott Mason Duncan, Madison, WI (US); Miguel Angel Pagan, Mount Hope, NY (US); Middleton Brawner Floyd, Jr., Suffern, NY (US)

(73) Assignee: Wyeth Holdings Corporation, Madison, NJ (US)

( * ) Notice: Subject to any disclaimer, the term of this patent is extended or adjusted under 35 U.S.C. 154(b) by 67 days.

(21) Appl. No.: 10/820,115

(22) Filed: Apr. 7, 2004

(65) Prior Publication Data

US 2004/0204587 A1 Oct. 14, 2004

(Under 37 CFR 1.47)

Related U.S. Application Data

(60) Provisional application No. 60/461,647, filed on Apr. 9, 2003.

(51) Int. Cl.[7] ............................................. C07D 215/36
(52) U.S. Cl. ...................................................... 546/155
(58) Field of Search ......................................... 546/155

(56) References Cited

U.S. PATENT DOCUMENTS 6,002,008 A * 12/1999 Wissner et al. ............. 546/160

FOREIGN PATENT DOCUMENTS

WO    WO 98/43960    10/1998

* cited by examiner

*Primary Examiner*—Cecilia J. Tsang
*Assistant Examiner*—Binta Robinson
(74) *Attorney, Agent, or Firm*—Joy S. Goudie

(57) ABSTRACT

There is provided a process for the preparation of 3-cyano-6-alkoxy-7-nitro-4-quinolone intermediates useful for the preparation of protein tyrosine kinase (PTK) inhibitors which are useful in the treatment of cancer of the formula:

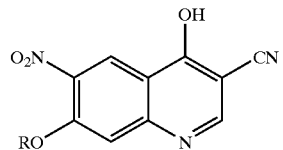

wherein R is alkyl($C_1$–$C_3$) prepared by reacting a substituted anthranilate with N,N-dimethylformamide dimethyacetal to obtain a N,N-dimethylamidine which is condensed with t-butylcyanoacetate to obtain a N-(2-cyano-2-t-butoxycarbonylvinyl)anthranilate, which is hydrolyzed to yield a N-(2-cyano-2-carboxyvinyl)anthranilate followed by decarboxylating to obtain a N-(2-cyano-2-carboxyvinyl) anthranilate followed by cyclizing to obtain a 3-cyano-6-alkoxy-7-nitro-4-quinolone.

34 Claims, No Drawings

PROCESS FOR THE SYNTHESIS OF 3-CYANO-6-ALKOXY-7-NITRO-4-QUINOLONES

This application claims priority from copending provisional application Ser. No. 60/461,647, filed Apr. 9, 2003, the entire disclosure of which is hereby incorporated by reference.

BACKGROUND TO THE INVENTION

This invention relates to a process for the large scale preparation of 3-cyano-6-alkoxy-7-nitro-4-quinolones, which are intermediates for the preparation of protein tyrosine kinase (PTK) inhibitors useful in the treatment of cancer.

The two most frequently used synthetic methods for the preparation of 3-cyano-4-quinolones or 3-carboalkyloxyquinolones are intramolecular Friedel-Crafts reactions and electrocyclic ring closures of N-(2-carboxyvinyl)-aniline derivatives. Friedel-Crafts conditions work well for electron rich anilines, moderately for unsubstituted anilines, and poorly or not at all for electron-deficient anilines and are especially not useful for large scale preparation of 3-cyano-4-quinolones utilizing electron deficient anilines. The electron withdrawing groups of the aniline reduce the nucleophilicity of the aromatic ring to the point that side reactions compete with, if not dominate, the desired intramolecular condensation. Thermal conditions for electrocyclic ring closures of N-(2-carboxyvinyl)-aniline derivatives typically require temperatures in excess of 240° C. However, the construction of 3-cyano-4-quinolones has been achieved by electrocyclic ring closure reactions of N-(2-carboxyvinyl) aniline derivatives by heating to 260° C. in diphenyl ether (U.S. Pat. No. 6,002,008; WO 98/43960). In particular, there are several deficiencies associated with electrocyclic ring closures for preparing quantities of material on a process scale. Typically, reactions are run at high dilution (66:1) resulting in an inefficient large-scale process due to low throughput. Further, thermal decomposition of either the final product and/or the starting material compromises the purity of the final product as a result of the high temperature reaction conditions. Additionally, equipment necessary to perform high temperature reactions safely on larger scale is expensive and not available in a typical laboratory or plant environment.

The production of 3-cyano-4-quinolones by electrocyclic ring closure suffers from all of the problems mentioned above, especially thermal decomposition of the desired final product or the starting material. For example, it is known that 7-ethoxy-4-hydroxy-6-nitroquinoline-3-carbonitrile decomposes at 240° C. while the minimum temperature required for cyclization is 256° C.

Thus, there is a need in the art for a process that addresses and preferably overcomes the high temperature cyclization, which results in thermal decomposition.

The following experimental details are set forth to aid in an understanding of the invention, and are not intended, and should not be construed to limit in any way the invention set forth in the claims that follow thereafter.

BRIEF SUMMARY OF THE INVENTION

This invention provides a process for the production of a 3-cyano-6-alkoxy-7 nitro-4-quinolone comprising:

a) reacting a substituted anthranilate of formula (I) with dimethylformamide dimethyl acetal:

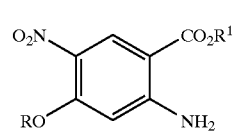

wherein R and $R^1$ are alkyl;
to obtain a compound of formula (II):

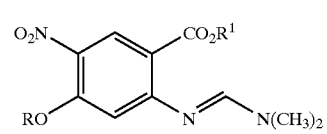

b) condensing the compound of step a) with t-butylcyanoacetate to obtain a compound of formula (III):

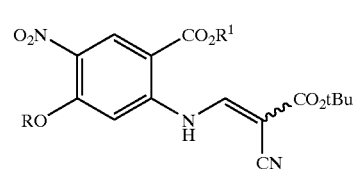

c) hydrolyzing the compound of step b) to yield compound of formula (IV):

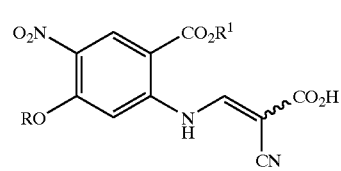

d) decarboxylating the compound of step c) to a compound of formula (V):

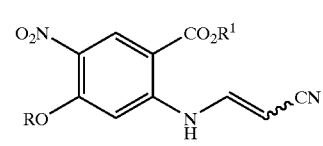

e) cyclizing the compound of step d) in the presence of a base to obtain a 3-cyano-6-alkoxy-7-nitro-4-quinolone of formula:

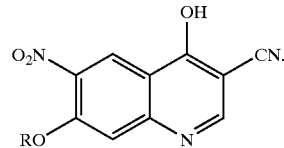

When used herein the term alkyl denotes a straight or branched chain alkyl group, e.g. a C1–C6 alkyl group, preferably a C1–C4 alkyl group, more preferably Me, Et, n-Pr, I—Pr, n-Bu, most preferably Me or Et. R and $R^1$ can be the same or different. The present invention encompasses all tautomeric forms of the compounds as well as mixtures of the tautomeric forms.

DETAILED DESCRIPTION OF THE INVENTION

The invention described herein for the production of 3-cyano-6-alkoxy-7-nitro-4-quinolones obviates the high temperature (256° C.) and the low throughput (66:1) high dilution issues hereinbefore described. These reaction conditions allow the cyclization reaction to be performed in standard processing equipment.

The process of the invention is shown in Scheme I.

butoxycarbonyl-vinyl)anthranilate 3. In a preferred embodiment condensation is conducted by the addition of t-butanol at about 25° C. to about 35° C. with about 1.5 to about 2.0 equivalents of t-butylcyanoacetate which provides high quality material (>98% high pressure liquid chromatography (HPLC area)) in high yield (90–99%).

The hydrolysis of the N-(2-cyano-2-t-butoxycarbonyl-vinyl)anthranilate 3 may be accomplished by the use of an acid in a solvent or using acetic acid directly as solvent at about 20° C. to about 110° C. In a preferred embodiment hydrolysis comprises treating N-(2-cyano-2-t-butoxycarbonyl-vinyl)anthranilate 3 with a catalytic amount of triflic acid in acetonitrile at about 20° C. to about 30° C.

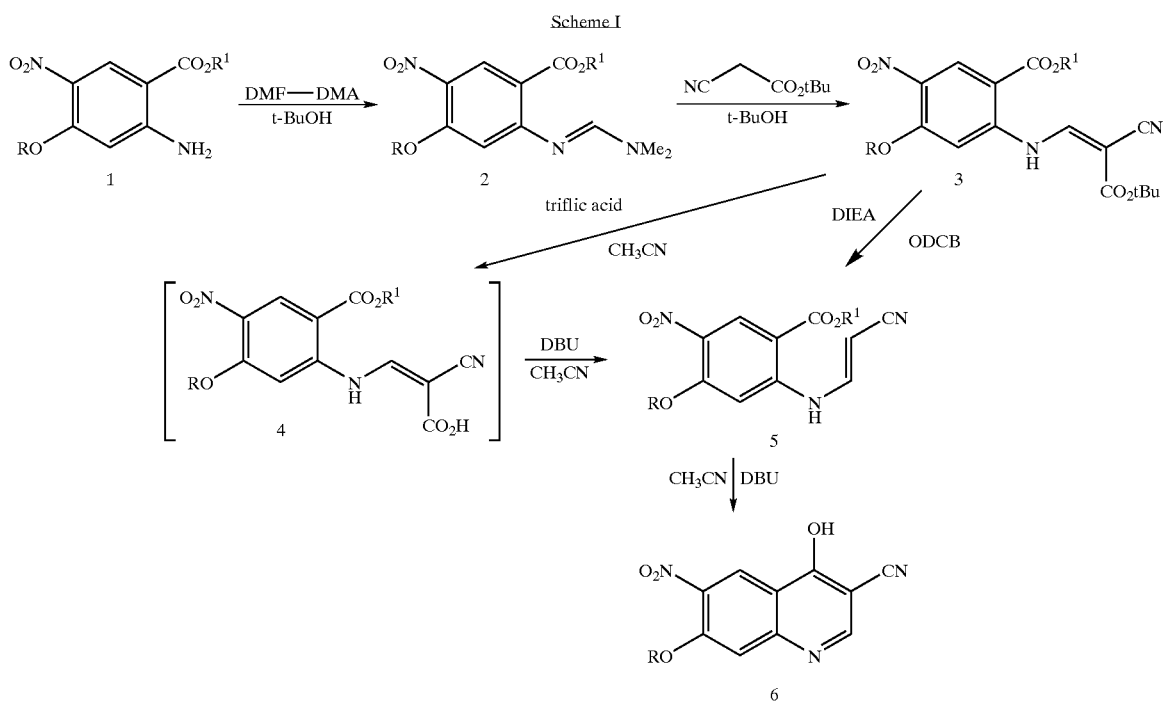

As described in Scheme I, substituted anthranilate 1 where R is alkyl, is reacted with dimethylformamide dimethyl acetal (DMF-DMA) or with about 1 to 5 equivalents of dimethylformamide dimethyl acetal in a alcoholic solvent to yield N,N-dimethylamidine 2. In a preferred embodiment the concentration of (DMF-DMA) is 1 to 2 equivalents. Preferred conditions for this reaction use about 1.2 equivalents of dimethylformamide dimethyl acetal in t-butanol at about 50° C. to about 120° C. with a preferred temperature of 80° C. In a preferred embodiment the reaction allows for simple isolation of N,N-dimethylamidine 2 by cooling the reaction mixture to allow the product to precipitate and collecting the precipitate by filtration. This procedure provides a near quantitative yield of N,N-dimethylamidine 2 of sufficient purity for use in the subsequent step without further purification. In an additionally preferred procedure substituted anthranilate 1 is reacted with dimethylformamide dimethyl acetal at reflux (about 110° C.) and the N,N-dimethylamidine 2 isolated after dilution with water, by filtering and drying the collected product.

The condensation reaction of N,N-dimethylamidine 2 with t-butylcyanoacetate may be performed using acetonitrile, acid, toluene, or alcoholic solvent at about 20° C. to about 110° C. to obtain N-(2-cyano-2-t- to produce N-(2-cyano-2-carboxyvinyl)anthranilate 4 as characterized by NMR. The N-(2-cyano-2-t-butoxycarbonyl-vinyl)anthranilate 3 may optionally be heated to 180° C. in o-dichlorobenzene (ODCB) to remove the t-butyl ester and afford N-(2-cyano-2-carboxyvinyl) anthranilate 4.

The decarboxylation of N-(2-cyano-2-carboxyvinyl) anthranilate 4 may be accomplished under either acidic or basic conditions to yield N-(2-cyano-vinyl)anthranilate 5. In a preferred embodiment acids include acetic acid and p-toluenesulfonic acid, bases include diisopropylethylamine, pyridine, or diazobicyclo[2.2.3] undecene (DBU), in suitable solvents which include acetonitrile, acetic acid, pyridine, and dimethylacetamide at about 80° C. to about 140° C. If the thermally induced hydrolysis of N-(2-cyano-2-t-butoxycarbonyl-vinyl) anthranilate 3 to N-(2-cyano-vinyl)anthranilate 5 in o-dichlorobenzene (ODCB) is performed in the presence of a catalytic amount of a suitable base which includes diisopropylethylamine(DIEA) then N-(2-cyano-2-t-butoxycarbonyl-vinyl)anthranilate 3 is converted directly to N-(2-cyano-vinyl)anthranilate 5. In a preferred embodiment DBU in acetonitrile at about 80° C. is used.

The intramolecular anionic cyclization (cyclizing) of N-(2-cyano-vinyl)anthranilate 5 to 3-cyano-6-alkoxy-7- nitro-4-quinolone 6 may be accomplished with about 2 to 13 equivalents of base in solvent. In a preferred embodiment the base includes DBU, NaH, piperidine, dimethylaminopyridine (DMAP) or potassium t-butoxide (KotBu). In a preferred embodiment solvents include acetonitrile, diphenylether, ODCB, THF/xylene mixtures, toluene, N,N-dimethylformamide (DMF), propionitrile or isopropanol. In a preferred embodiment dilution ratios of solvent:substrate are about 15 to about 30:1 at about 60° C. to about 140° C. The preferred procedure to prepare 3-cyano-6-alkoxy-7-nitro-4-quinolone 6 is to treat N-(2-cyano-vinyl)anthranilate 5 with about 3 to 5 equivalents of DBU in acetonitrile at about 80° C. for about 4 to 5 hours and quenching with aqueous HCl.

A more preferred procedure to produce 3-cyano-6-alkoxy-7-nitro-4-quinolone 6 from N-(2-cyano-2-t-butoxycarbonyl-vinyl)anthranilate 3 is to conduct the hydrolysis, decarboxylation and intramolecular cyclization reaction sequentially in the same vessel without isolation of N-(2-cyano-2-carboxyvinyl)anthranilate 4 or N-(2-cyano-vinyl)anthranilate 5. The more preferred process for producing 3-cyano-6-alkoxy-7-nitro-4-quinolone 6 is comprised of hydrolyzing N-(2-cyano-2-t-butoxycarbonyl-vinyl) anthranilate 3 with about 0.2 to about 0.3 equivilents of triflic acid in acetonitrile at about 20° C. to about 30° C. for about 5 to 60 min followed by the addition of about 3 to 5 equivalents of DBU and refluxing the reaction mixture for about 4 to 5 hours. The 3-cyano-6-alkoxy-7-nitro-4-quinolone 6 is isolated by diluting the reaction mixture with water and collecting the resulting precipitate by filtration. The collected precipitate is triturated with ethyl acetate to provide 3-cyano-6-alkoxy-7-nitro-4-quinolone 6 as beige to brown solid (70–80% yield, >98% by $^1$H NMR).

The invention claimed herein provides 3-cyano-7-alkoxy-6-nitro-4-quinolones by combining steps and without the need for high temperature cyclization. 3-Cyano-6-alkoxy-7-nitro-4-quinolone 6 is provided in good overall yield (70% for 5 transformations performed in two single reactor operations, with purity >98% by HPLC and $^1$H NMR).

For purposes of this invention an acid is a molecular entity or chemical species capable of donating a proton or capable of forming a covalent bond with an electron pair. Preferred acids include acetic acid, trifluoroacetic acid, p-toluenesulfonic acid, methanesulfonic acid and triflic acid.

For purposes of this invention a solvent is the term applied to the whole initial liquid phase containing the extractant. The solvent may contain only one extractant or it may be a composite homogeneous mixture of extractant(s) with diluent(s). In a preferred embodiment the solvent includes toluene, acetonitrile, tetrahydrofuran (THF), dimethylacetamide, acetic acid, pyridine, diphenylether, ODCB, THF/xylene mixtures, toluene, N,N-dimethylformamide (DMF), propionitrile or isopropanol.

For purposes of this invention a base is a chemical species or molecular entity having an available pair of electrons capable of forming a covalent bond with a proton or with the vacant orbital of some other species. In a preferred embodiment a base includes diisopropylethylamine, pyridine, or diazobicyclo[2.2.3]undecene (DBU), NaH, piperidine, dimethylaminopyridine (DMAP) or potassium t-butoxide (KOtBu).

For purposes of this invention the term "alkyl" includes both straight and branched alkyl moieties, preferably of 1 to 6 carbon atoms.

In order to facilitate a further understanding of the invention, the following non-limiting examples illustrate the process of the present invention.

EXAMPLE 1

2-[[(Dimethylamino)methylene]amino]-4-ethoxy-5-nitrobenzoic acid, methyl ester

A 3-L round-bottomed flask under $N_2$ equipped with an overhead stirrer, a condenser and a thermocouple is charged with 2-amino-4-ethoxy-5-nitrobenzoic acid methyl ester (80 g, 333 mmol) and N,N-dimethylformamide dimethyl acetal (500 mL). The reaction mixture is heated to reflux (100° C.). Once the thick slurry becomes homogeneous and the reaction is complete, the reaction mixture is cooled to 25 to 30° C. The reaction mixture is diluted with water (3 L) and the resulting suspension is filtered. The filter cake is washed with water (3×500 mL) and dried under vacuum (50 mm Hg) at 55° C. to provide the title compound as an off-white solid (89.6 g, 91% yield, >90% purity by NMR integration). $^1$H NMR (300 MHz, DMSO-$d_6$): 8.23 (s, 1H), 7.81 (s, 1H), 6.71 (s, 1H), 4.22 (q, J=7 Hz), 3.68 (s, 3H), 3.09 (s, 3H), 2.97 (s, 3H), 1.40 (t, J=7 Hz, 3H).

EXAMPLE 2

2-Cyano-3-(5'-ethoxy-2'-methoxycarbonyl-4'-nitrophenyl)amino-2-propenoic acid t-butyl ester A 3-L round-bottomed flask under $N_2$ equipped with an overhead stirrer, a condenser and a thermocouple is charged with 2-[[(dimethylamino)methylene]amino]-4-ethoxy-5-nitrobenzoic acid, methyl ester (68 g, 230 mmol), t-butanol (500 mL) followed by t-butylcyanoacetate (65 g, 460 mmol). The reaction mixture is heated to reflux. After 4 hours the reaction is cooled to room temperature and the suspension is filtered. The filter cake is washed with heptane (2×100 mL) and dried under vacuum (50 mm Hg) at 40° C. to provide the title compound as a beige solid (83 g, 91% yield, >98% purity by NMR). $^1$H NMR (300 MHz, DMSO-$d_6$): 12.7 (d, J=12.9 Hz, 1H), 8.77 (d, J=12.9 Hz, 1H), 8.50 (s, 1H), 7.47 (s, 1H), 4.37 (q, J=7 Hz, 2H), 3.91 (s, 3H), 1.52 (s, 9H), 1.40 (t, J=7 Hz, 3H).

EXAMPLE 3

2-Cyano-3-(5'-ethoxy-2'-methoxycarbonyl-4'-nitrophenyl)amino-2-propenoic acid t-butyl ester A 3-L round-bottomed flask under $N_2$ equipped with an overhead stirrer, a condenser and a thermocouple is charged with 2-amino-4-ethoxy-5-nitrobenzoic acid methyl ester (100 g, 0.416 mol) and N,N-dimethylformamide dimethyl acetal (59.5 g, 0.499 mol) and t-butanol (800 mL). The reaction mixture is heated to reflux for 1.5 h. The reaction mixture is cooled to 22 to 35° C. and the t-butylcyanoacetate (117 g, 0.832 mol) added. The reaction mixture is stirred at 20 to 30° C. for 2 h. The precipitate is collected by suction filtration, washed with heptane (500 mL), then dried to constant weight under reduced pressure (50 mm Hg)) at 45° C. overnight to provide the title compound as a off-white solid (162.9 g, 95% yield, >95% purity by HPLC). $^1$H NMR (300 MHz, DMSO-$d_6$): 12.7 (d, J=12.9 Hz, 1H), 8.77 (d, J=12.9 Hz, 1H), 8.50 (s, 1H), 7.47 (s, 1H), 4.37 (q, J=7 Hz, 2H), 3.91 (s, 3H), 1.52 (s, 9H), 1.40 (t, J=7 Hz, 3H).

EXAMPLE 4

N-(2-cyanvinyl)-2-amino-4-ethoxy-5-nitrobenzoic Acid

A 500-mL round-bottomed flask under $N_2$ equipped with a stirbar, a condenser and a thermocouple is charged with (Z)-2-Cyano-3-(5'-ethoxy-2'-methoxycarbonyl-4'-nitrophenyl)amino-2-propenoic acid t-butyl ester (20 g, 51.1 mmol), N,N-diisopropylethylamine (1 mL, 5.72 mmol) and o-dichlorobenzene (200 mL). The reaction is heated to reflux (180° C.). After 7.5 hours the reaction was complete as evidenced by thin layer chromatography. The reaction is cooled to room temperature and dilute hexane (500 mL) to precipitate the crude product. The solid is isolated by filtration to provide the title compound as a beige powder (11.7 g, 79% yield of 65:35 stereoisomers, 94% purity by NMR). $^1$H NMR (300 MHz, DMSO-$d_6$): 11.1 (d, J=12.7 Hz, 0.65H), 10.6 (d, J=12.9 Hz, 0.35H), 8.47 (s, 0.65H), 8.37 (s, 0.35H), 8.29 (dd, J=13.4, 12.9 Hz, 0.35H), 8.16 (dd, J=12.7, 8.5 Hz, 0.65H), 7.13 (s, 1H), 5.49 (d, J=13.4 Hz, 0.35H), 4.97 (d, J=8.4 Hz, 0.65H), 4.38–4.28 (m, 2H), 3.90 (s, 1.95H), 3.88 (s, 1.05H), 1.39 (t, J=7 Hz, 3H).

EXAMPLE 5

7-ethoxy-4-hydroxy-6-nitroquinoline-3-carbonitrile

A 100-mL round-bottomed flask equipped with an overhead stirrer, a condenser and a thermocouple is charged with (Z)-2-Cyano-3-(5'-ethoxy-2'-methoxycarbonyl-4'-nitrophenyl)amino-2-propenoic acid t-butyl ester (2.5 g, 6.3 mmol) and acetonitrile (50 mL). The triflic acid (0.12 mL, 0.21 mmol) is added to the heterogeneous reaction medium. Upon disappearance of the starting material as evidenced by TLC (20% EtOAc/hexane), the DBU (4.0 mL, 4.25 mmol) is added to the reaction mixture. The reaction is then heated to reflux and monitored for completion (>95% by HPLC—Phenomenex 3 micron Phenyl-hexyl column (150×4.6 mm)). The reaction is then quenched with 10% HCl (100 mL) and diluted with water (400 mL). After stirring for 15 minutes at room temperature the suspension is filtered and the collected solid allowed to "air" dry. The collected solid is suspended in ethyl acetate (25 mL) at room temperature and filtered again and allowed to "air" dry. This procedure provides 1.15 g (70%) of the title compound as a beige solid that is >95% product by NMR integration. $^1$H NMR (300 MHz, DMSO-$d_6$): 12.9 (s, 1H), 8.79 (s, 1H), 8.51 (s, 1H), 7.24 (s, 1H), 4.27 (q, J=7 Hz, 2H), 1.41 (t, J=7 Hz, 3H).

What is claimed:

1. A process for the production of a 3-cyano-6-alkoxy-7-nitro-4-quinolone comprising:

a) reacting a substituted anthranilate of formula (I) with dimethylformamide dimethyl acetal:

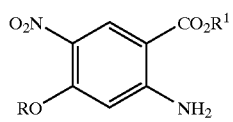

(I)

wherein R and $R^1$ is an alkyl;
to obtain a compound of formula (II):

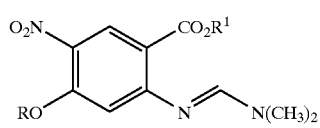

(II)

b) condensing the compound of formula (II) with t-butylcyanoacetate to obtain a compound of formula (III):

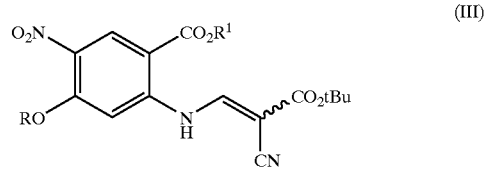

(III)

c) hydrolyzing the compound of formula (III) to yield compound of formula (IV):

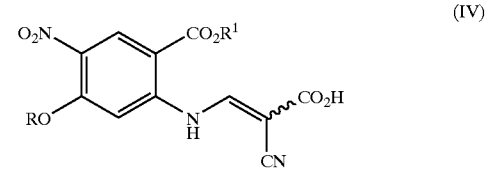

(IV)

d) decarboxylating the compound of formula (IV) to a compound of formula (V):

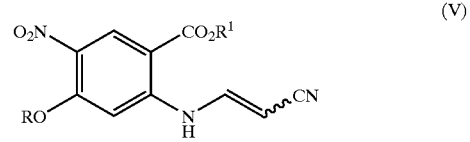

(V)

e) cyclizing the compound of formula (V) to obtain a 3-cyano-6-alkoxy-7-nitro-4-quinolone of formula:

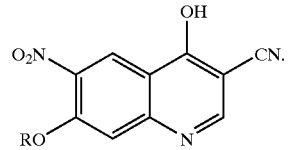

2. The process of claim 1 wherein the reacting of the compound of formula (I) and dimethylformamide dimethyl acetal with an alcoholic solvent at a temperature of about 50° C. to about 80° C.

3. The process of claim 2 wherein the alcoholic solvent is t-butanol.

4. The process of claim 1 wherein the reacting is at about 80° C.

5. The process of claim 1 wherein in step a) the reacting is cooled until the compound of formula (II) precipitates out.

6. The process of claim 1 wherein the dimethylformamide dimethyl acetal and anthranilate react without alcoholic solvent and heated to about 110° C. to yield the compound of formula (II).

7. The process of claim 6 wherein the reaction mixture is diluted, filtered and dried to obtain the compound of formula (II).

8. The process of claim 1 wherein the dimethylformamide dimethylacetal is present in a concentration of 1 to 5 equivalents.

9. The process of claim 8 wherein the dimethylformamide dimethylacetal is present in a concentration of 1 to 2 equivalents.

10. The process of claim 9 wherein the dimethylformamide dimethylacetal is present in a concentration of 1.2 equivalents.

11. The process of claim 1 wherein the condensing comprises combining the compound of formula (II), acetonitrile, an acid, toluene or alcoholic solvent to obtain a compound of formula (III) at a temperature of about 20° C. to about 110° C.

12. The process of claim 11 wherein the acid is selected from the group consisting of acetic acid, trifluoroacetic acid, p-toluene sulfonic acid, methanesulfonic acid, or triflic acid.

13. The process of claim 12 wherein the acid is acetic acid.

14. The process of claim 1 wherein the condensing comprises addition of alcoholic solvent in combination with t-butylcyanoacetate at a temperature of about 25° C. to about 35° C.

15. The process of claim 14 wherein the alcoholic solvent is t-butanol.

16. The process of claim 14 wherein the butanol is about 1.5 to about 2.0 equivalents of butylcyanoacetate.

17. The process of claim 1 wherein the hydrolyzing comprises addition of acid in a solvent to the compound of formula (III) at a temperature of about 20° C. to about 110° C.

18. The process of claim 17 wherein the acid is selected from acetic acid, trifluoroacetic acid, p-toluene sulfonic acid, methanesulfonic acid, or triflic acid.

19. The process of claim 17 wherein the solvent is selected from toluene, acetonitrile, tetrahydrofuran, dimethylacetamide.

20. The process of claim 17 wherein the acid and the solvent is acetic acid.

21. The process of claim 17 wherein the hydrolyzing comprises addition of triflic acid in acetonitrile to the compound of formula (III) at a temperature of about 20° C. to about 30° C.

22. The process of claim 1 wherein the decarboxylating comprises addition of an acid or base to the compound of formula (IV) in a solvent at a temperature of about 80° C. to about 140° C.

23. The process of claim 22 wherein the solvent is selected from toluene, acetonitrile, tetrahydrofuran, dimethylacetamide, diphenylether, o-dichlorobenzene, THF/xylene mixture, dimethyl propionitrile, and isopropanol.

24. The process of claim 22 wherein the acid is selected from acetic acid, trifluoroacetic acid, p-toluene sulfonic acid, methanesulfonic acid, or triflic acid.

25. The process of any one of claim 22 wherein the base is selected from diisopropylethylamine, pyridine, diazobicyclo[2.2.3]undecene, sodium hydroxide, piperidine, dimethylformamide, propionitrile or isopropanol.

26. The process of claim 22 comprising addition of diazobicyclo[2.2.3]undecene and acetonitrile to the compound of formula (IV) at a temperature of about 80° C.

27. The process of claim 1 wherein the cyclization comprises addition of a base in a solvent to a compound of formula (V) at a temperature of about 60° C. to about 140° C. for about 4 to 5 hours.

28. The process of claim 27 wherein the base is selected from diisopropylethylamine, pyridine and diazobicyclo[2.2.3]undecene, sodium hydroxide, piperidine, dimethylformamide, propionitrile or isopropanol.

29. The process of claim 27 wherein the solvent is selected from toluene, acetonitrile, tetrahydrofuran, dimethylacetamide, diphenylether, o-dichlorobenzene, THF/xylene mixture, dimethyl propionitrile, and isopropanol.

30. The process of claim 27 wherein the cyclization comprises addition of diazobicyclo[2.2.3]undecene in acetonitrile at about 80° C. for about 4 to 5 hours to obtain 3-cyano-6-alkoxy-7-nitro-4-quinolone.

31. The process of claim 30 wherein diazobicyclo[2.2.3] undecene is 3 to 5 equivalents.

32. The process of claim 30 wherein the 3-cyano-6-alkoxy-7-nitro-4-quinolone is isolated by quenching with aqueous HCl.

33. The process of claim 1 wherein the hydrolysis, decarboxylation, and cyclization are performed sequentially without isolation.

34. The process of claim 33 comprising hydrolyzing the compound of formula (III) with triflic acid in acetonitrile at about 20° C. to about 30° C. for a maximum of 60 minutes, adding DBU and refluxing for up to 5 hours.

* * * * *